United States Patent [19]

Phillips et al.

[11] Patent Number: 4,689,319

[45] Date of Patent: Aug. 25, 1987

[54] ORAL ENERGY RICH THERAPY FOR DIARRHEA IN MAMMALS

[75] Inventors: Robert W. Phillips; Jerald A. Ellinghuysen, both of Ft. Collins, Colo.

[73] Assignee: Colorado State University Research Foundation, Fort Collins, Colo.

[21] Appl. No.: 730,267

[22] Filed: May 6, 1985

Related U.S. Application Data

[63] Continuation of Ser. No. 457,829, Jan. 13, 1983, abandoned.

[51] Int. Cl.⁴ .............................................. A61K 31/70
[52] U.S. Cl. ...................................................... 514/25
[58] Field of Search ......................................... 514/25

[56] References Cited

U.S. PATENT DOCUMENTS 2,139,139 12/1938 Tompkins ........................... 424/180
3,928,574 12/1975 Phillips .............................. 424/180
4,164,568 8/1979 Bywater ............................. 424/180

Primary Examiner—Johnnie R. Brown
Attorney, Agent, or Firm—Edwin L. Spangler, Jr.

[57] ABSTRACT

A hyperosmotic oral veterinary composition in liquid form that provides easily absorbed and metabolized energy substrates comprising 70 to 90 percent of an actively absorbed monosaccharide, 1 to 7.5 percent of an actively absorbed naturally occurring amino acid, 0.1 to 5 percent of citric acid, 4 to 12 percent of a non-toxic alkali metal salt of acetic acid which, when diluted with water for administration and is present in a concentration of 30–90 grams per liter useful for the treatment of diarrhea in animals such as calves.

23 Claims, 4 Drawing Figures

THERAPY RESPONSE

GLUCOSE BLOOD LEVELS BY TIME POST-DOSE

CHANGE IN BUN DURING THE COURSE OF THERAPY

ORAL ENERGY RICH THERAPY FOR DIARRHEA IN MAMMALS

This application is a continuation of application Ser. No. 457,829, filed Jan. 13, 1983, now abandoned.

FIELD OF THE INVENTION

Diarrheal diseases in mammals cause severe dehydration and electrolyte-energy imbalances. The instant invention concerns a therapy which restores the electrolytes which have been lost and, in addition, provides a sufficiency of energy substrates in a readily absorbable and utilizable form.

BACKGROUND OF THE INVENTION

Several prior investigators have been concerned with diarrheal diseases. These investigators have proposed oral therapeutic intervention to reduce the serious impact of diarrheal diseases. Generally, these systems are directed primarily toward solving the problem of dehydration and, in some cases, to providing electrolytes and a minimal amount of energy sources such as glucose. However, the principle reason for including organic molecules which might provide some energy has been to enhance absorption. It is generally believed today that oral fluids must be supplied as essentially isoosmotic fluids (approximately 300 mOsm/l) since that is the concentration of solute in body fluids. Hyperosmotic fluids are considered detrimental since they are believed to cause increased secretion. This is brought out in a paper by R. J. Bywater entitled: Pathosphysiology and Treatment of Calf Diarrhea, *Proceedings XII World Congress of Diseases of Cattle*, Amsterdam, Sept. 1982, pp. 291-297. In discussing oral therapy for diarrhea, Dr. Bywater reiterated that "solutions for this purpose should be approximately isotonic (300 mOsm/kg) since, before they can be absorbed, hypertonic solutions must first become isotonic,". In another paper presented at the same World Congress by C. Demigne, C. Remesy and F. Chartier entitled: Interest of Acetate in Oral Glucose-electrolytes Formulations for Treatment of Dehydration in Diarrheic Calves, *Proceedings XII World Congress of Diseases in Cattle*, Amsterdam, Sept. 1982, pp. 305-309, it is stated "Osmolarity is also an important factor, the optimum being possible in the range of 300 to 350 mOsm". However, if an isotonic fluid is given, some benefit is derived, but an insufficient amount of energy or electrolytes or both will be provided to the diarrheic animal. This is a particularly serious problem in young neonates who have a greater tendency to become diarrheic. In another paper in this field, G. Alexander, N. W. Bennett and R. T. Gemmell, discuss Brown Adipose Tissue in the Newborn Calf (*Bos taurus J. Physiol.* 244:223-234, 1975, and state that young neonates do not have sufficient energy reserves in their body. In addition, these animals have difficulty in mobilizing the energy that is present.

U.S. Pat. No. 3,898,328 to Beigler et al, describes a dry stable composition for the treatment of scours and dehydration, and U.S. Pat. No. 4,164,568 to Bywater, describes an oral scour formulation with citrate. These oral products provide only 20-30% of the animal's basic maintenance energy requirement and, therefore, will contribute to continuing body weight loss and energy deficit.

In my U.S. Pat. No. 3,928,574, I disclose a method and composition for treating diarrhea in bovine animals. The composition consists of sodium chloride, a potassium salt and glucose in aqueous solution. The solutions are buffered to maintain a basic condition, such that pH does not exceed 10. These solutions are formulated for use intravenously or subcutaneously. The formulation described in this patent does not include acetate for rapid energy and absorption, nor glycine and citric acid.

A prominent clinical sign of diarrhea is acidosis due to intestinal bicarbonate loss, anerobic metabolism and decreased renal function. Blood bicarbonate levels are often decreased by 50%. The prior art investigators contend that acidosis may be corrected by providing organic acids alone which will be converted by bicarbonate. However, this is not the case, for metabolism of organic acid leads only to the production of carbon dioxide. It is critically necessary to supply sufficient sodium ion or other alkali metal cations as a salt of the organic acid. The metabolism of that acid will provide one bicarbonate for every monovalent cation such as sodium.

For example:

1 citric acid on oxidation $\longrightarrow$ 6 $CO_2$

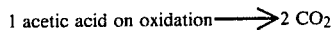

1 acetic acid on oxidation $\longrightarrow$ 2 $CO_2$

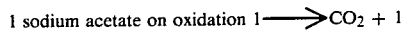

1 sodium acetate on oxidation 1 $\longrightarrow$ $CO_2$ + 1

sodium bicarbonate ($NaHCO_3$)

SUMMARY OF THE INVENTION

I have found that contrary to the teaching of the prior investigators, when dealing with oral therapy, a formulation consisting of an actively absorbed monosaccharide, an actively absorbed naturally occurring amino acid, citric acid, a non-toxic alkali metal salt of acetic acid, inorganic salts such as sodium chloride and potassium chloride, when prepared in dry form and added to water prior to use, can be used to make a hypertonic oral solution which should be from 600 to 1200 mOsm/l or 2 to 4 times normal body osmolality. The formulation provides an adequate easily absorbed metabolized substrate and the energy substrate, as administered, provides 50 to 110% of the calve's maintenance energy requirements. The major component of this formulation is the monosaccharide as it provides the most usable energy per Osmole. There is also a significant quantity of a non-toxic alkali metal salt of acetic acid which is most rapidly utilized for immediate energy following absorption and, thus, provides a very immediate energy supply and also an immediate source of bicarbonate. The metabolism of the acetate in the body is over 5 times as fast as the metabolism of glucose on a molar basis and, thus, provides immediate energy as well as bicarbonate.

DETAILED DESCRIPTION OF THE INVENTION

Figure 1:
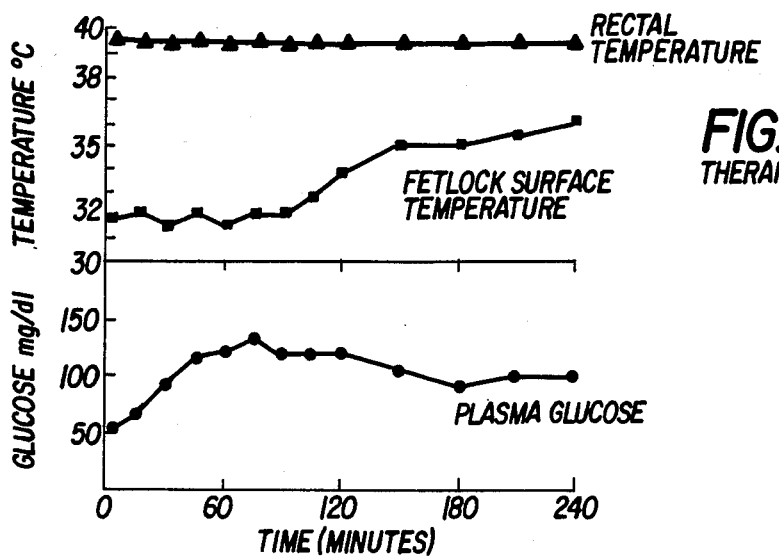
FIG. 1 shows the therapy response based on rectal temperature and fetlock surface temperature as a function of time and plasma glucose concentration.

The easily absorbed and metabolized composition useful in treatment of diarrhea in animals comprises 70 to 90 percent of an actively absorbed monosaccharide, which, when diluted with water for administration, is present at a concentration of 30 to 90 grams per liter, 1 to 1.75 percent of an actively absorbed naturally occurring amino acid, 0.1 to 5 percent of citric acid, 4 to 12 percent of a non-toxic alkali metal salt of acetic acid which, when diluted with water for administration, is present at a concentration of 3 to 12 grams per liter and 3 to 8 percent of inorganic salts such as sodium chloride and potassium chloride. The sum of the sodium and potassium is 120 to 160 mOsm per liter with the potassium being present as 10 to 30 mOsm per liter and the sodium 110 to 150 msO per liter. Examples of suitable actively absorbed monosaccharides include dextrose and galactose.

The actively absorbed natural occurring amino acid includes glycine and related compounds. Examples of non-toxic alkaline metal salt of acetic acid are sodium acetate, potassium acetate and lithium acetate. When these formulations are prepared and administered in the recommended quantities, they provide approximately 80% of the animal's energy requirements. Metabolism of the acetate component will yield a substantial amount of bicarbonate which can rapidly and significantly improve the bicarbonate condition of the diarrheic animal. This is an important factor, since it is widely recognized that diarrheic animals are acidotic with low bicarbonate levels. The present invention is illustrated by the following specific but non-limiting examples.

EXAMPLE I

A formulation was prepared containing the following components:

TABLE I

|  | % | Gram | Kcal/two liters | mOsm/l |
|---|---|---|---|---|
| Glucose | 81.8 | 130 | 520 | 361 |
| Glycine | 4.72 | 7.5 | 23 | 50 |
| Na Acetate | 6.20 | 9.84 | 18 | 120 |
| Citric Acid | .44 | .7 | 3 | 2 |
| NaCl | 4.42 | 7.02 | — | 120 |
| KCl | 2.43 | 3.72 | — | 50 |
| Water 2 liters |  |  | 564 | 703 |

The composition of remaining replacement fluid after metabolism of the organic constituents is set out in the Table below.

TABLE II

| Electrolytes | mEq/liter Invention | Normal Plasma | Diarrheic Plazma |
|---|---|---|---|
| Sodium | 120 | 135 | 135 |
| Potassium | 25 | 5 | 8 |
| Chloride | 85 | 100 | 100 |
| Bicarbonate (from acetate) | 60 | 25 | 15 |
| TOTAL | 290 |  |  |

The therapy therefore provides an extracellular fluid with added potassium and bicarbonate. This is important as most fluid is lost from the extracellular fluid pool.

The hematocrit declined rapidly in the first hour after therapy, and remained lower throughout the test as is shown in Table III.

TABLE III

|  | Changes after Therapy | | | |
|---|---|---|---|---|
|  | Pre | Hour 1 | Hour 2 | Hour 3-4 |
| Plasma Sodium mEq/l | 138.9 ± .3 | 140.3 ± 1.0 | 140.5 ± 0.6 | 139.9 ± 1.0 |
| Plasma Potassium mEq/l | 5.21 ± .20 | 4.59 ± 0.4 | 4.65 ± 10 | 4.56 ± 1.2 |
| Hematocrit % | 58.7 ± 1.3 | 51.2 ± 2.4 | 48.9 ± .4 | 50.7 ± 1.2 |

These data, when considered with the lack of change in plasma sodium concentration, provide firm evidence that secretion into the gastrointestinal tract and hemoconcentration were not occurring. The animal was hypoglycemic with a very low blood glucose (55 mg/dl) prior to therapy indicating a precarious energy state. Plasma glucose began to increase within 15 minutes of therapy and remained elevated for the duration of the test. The plasma glucose was still at 100 mg/dl four hours after therapy indicating a sustained benefit. Minor hyperkalemia was corrected. This data is confirmed in Table III above. FIG. 1 is a graphic illustration of the benefit of this therapy. It shows the restoration of normal fluid and energy metabolism as seen by the increase of skin temperature on the extremities without modification of rectal temperature. The increase in extracellular fluid volume including blood, allowed for normal blood circulation pattern to be reestablished and, as blood flow to the limbs was increased, their temperature increased.

EXAMPLE II

This example compares the beneficial effects of the formulation set out in Table I with the formulation set out in U.S. Pat. No. 4,164,568 consisting of the following composition:

TABLE IV

| Formulation of U.S. Pat. No. 4,164,568 | | | | |
|---|---|---|---|---|
|  | % | gram | kcal/2 liters | Osm/l |
| Glucose | 69.9% | 44.6 | 178 | 124 |
| Glycine | 9.7% | 6.2 | 19 | 41 |
| Citric A | 0.8% | .5 | 3 | 1 |
| $K_3$ Citrate | .2% | .1 | — | <1 |
| NaCl | 13.3% | 8.5 | — | 145 |
| $KH_2PO_4$ | 6.4% | 4.1 | — | 30 |
| 2 liters $H_2O$ |  |  | 200 | 342 |

The composition of remaining replacement fluid after metabolism of the organic constituents is set out in the table below.

TABLE V

| | U.S. Pat. No. 4,164,568 | mEq/liter normal plasma | diarrheic plazma |
|---|---|---|---|
| Sodium | 72 | 135 | 135 |
| Potassium | 15 | 5 | 8 |
| Chloride | 72 | 100 | 100 |
| Bicarbonate (from K₃ Citrate) | <1 | 25 | 15 |
| Phosphate | 15 | 5 mg/100 mls | 5 mg/100 mls |
| TOTAL | 175 | | |

This formulation is a commercially available product and was used according to label directions. Both the formulations set out in Table I and the formulation covered in U.S. Pat. No. 4,164,568 were administered as two quart doses to neonatal diarrheic calves less than 75 lbs and 3 quart doses to neonatal calves greater than 75 lbs twice a day for two days. After the end of the two-day period, the dosage was changed to a mixture of equal quantities of the therapy fluid with whole cows milk. During the first two days of therapy, when the products were administered alone, the efficacy can be more clearly delineated. One of the principle advantages of the therapy of the instant application is that the hyperosmotic solutions enhance net absorption. This is contrary to current thought as is pointed out above. The effect is shown by following the concentration of stable components in the blood plasma, which reflect this effect. This data is set out in Table VI.

TABLE VI

Changes in plasma protein concentration one hour following therapy.

| | pretherapy | 1 hour post | decrease |
|---|---|---|---|
| Formulation of Table I | 4.9 ± 0.3 | 4.6 ± 0.4 | −.3 |
| Formulation of Table IV | 4.8 ± 0.3 | 4.6 ± 0.2 | −.2 |

If the formulation of the instant invention causes proteins to become more concentrated, then net secretion, not net absorption, has occurred. However, the formulation of the instant invention, on the average, caused more dilution of plasma proteins in the first hour after administration than the formulation covered in U.S. Pat. No. 4,164,568. This phenomenon demonstrates rapid net absorption as further evidence of rapid absorption by the diarrheic calves.

Figure 2:
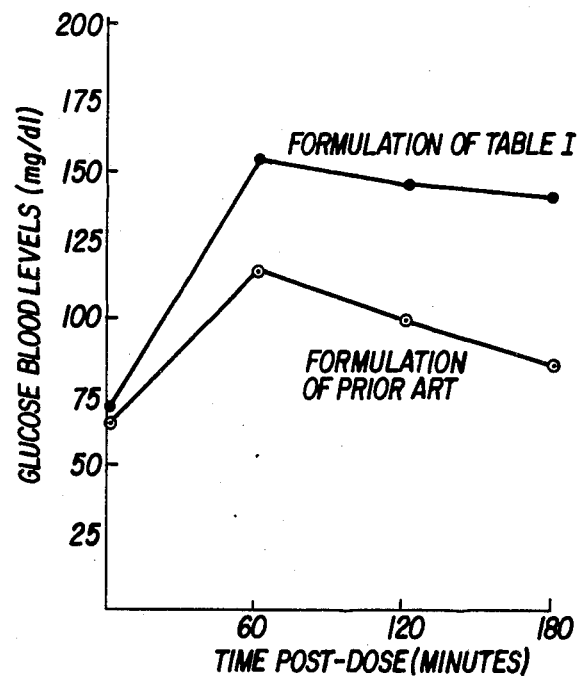
FIG. 2 is a graph of the glucose blood level relating to time after dose and compares the formulation of the current invention with the formulation of the prior art as set forth in U.S. Pat. No. 4,164,568.

The average increase in plasma glucose at the end of the first hour by the calves given the formulation of the instant invention was 104 mg/dl. In contrast, the calves receiving the formulation covered by the patent set out above had an average increase of only 53 mg/dl. By the end of 3 hours, the average elevation of plasma glucose above pretherapy levels in the calves receiving the formulation of the instant invention was 70 mg/dl versus only 20 mg/dl for the therapy using the formulation described in U.S. Pat. No. 4,164,568. This data is shown graphically in FIG. 2. This continuing three-fold elevation emphasizes the sustaining longer term benefits of the formulation of the instant invention in supplying much needed readily available energy to the initially energy deficient hypoglycemic calves.

EXAMPLE III

This example illustrates the further benefit of the increased availability of metabolizable glucose in the therapy of the present invention as compared to the therapy of the formulation covered in the above-identified patent. This benefit is shown in Table VII.

TABLE VII

Plasma potassium changes due to therapy:

| | K (mEq/l) pretherapy | 3 hours following therapy change in K (mEq/l) |
|---|---|---|
| Formulation of Table I | 5.3 ± .6 | −1.1 ± 0.5 |
| Formulation of Table IV | 5.0 ± .4 | −0.1 ± 0.3 |

All animals were hyperkalemic prior to therapy. Three hours following the therapy the decrease in plasma potassium averaged 1.1±0.5 mEq/l for the calves receiving the therapy of the formulation of the instant invention and all were within the normal range. In contrast, the calves receiving the therapy covered in the patent set out above had only minimal 0.1±0.3 mEq/l decrease, and several remained hyperkalemic.

Figure 3:
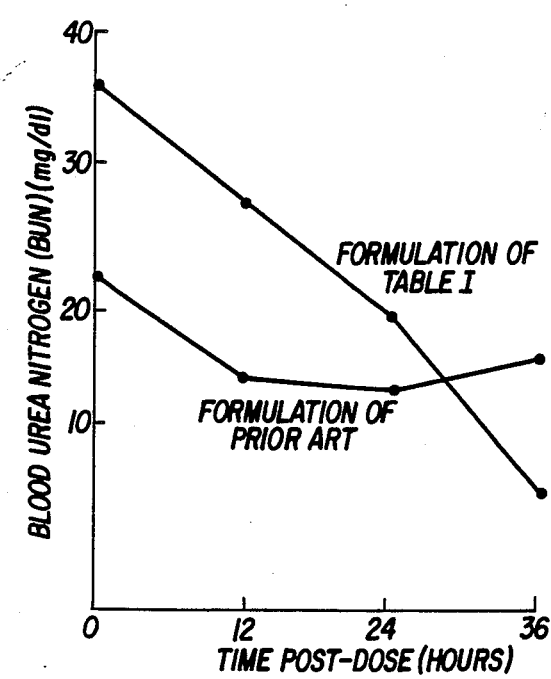
FIG. 3 is a graph of the changes in blood urea nitrogen during the course of therapy and compares formulation of the current invention with the formulation set forth in U.S. Pat. No. 4,164,568.

In addition, the mean blood urea nitrogen decreased precipitously following the initiation of the treatment of the instant application. Prior to the first therapy, the blood urea nitrogen was 35 mg/dl and was in the normal range at 9 mg/dl for 1½ days prior to the 4th therapy. This data is shown in FIG. 3. A decrease of blood urea nitrogen of this magnitude may be due to enhanced renal function allowing a more normal excretory pattern or may be due to a decrease in the catabolism of protein due to the provision of ample energy substrates. All calves treated with the formulation of the instant invention had blood urea nitrogen levels in a normal range in the last one-half of the experiment. FIG. 3 graphically compares the changes in the blood urea nitrogen during the course of therapy with the formulation of the current invention and with the formulation of U.S. Pat. No. 4,164,568.

One of the best indications of the long-term benefit of the therapeutic approach of the instant invention is the maintenance of body weight during therapy. This data is set out in Table VIII.

TABLE VIII

Change in body weight (lbs) following therapy:

| | Formulation of Table I | Formulation of Table IV |
|---|---|---|
| 2 days* | +1.5 | 0 |
| 4 days** | +4.5 | 1 |

*received therapy alone
**sum of all 4 days: in the last two days received 50% whole milk and 50% therapy.

When the calves received the therapy of the instant invention alone, the calves gained some weight. The gain was more pronounced in the last 2 days when the formulation was changed to 50% milk and 50% of the formulation in Table I. In this case, the animals received energy for maintenance as well as growth. In the first two days, it is likely that the gain in weight was due to rehydration without body wasting. The formulation of the prior art undoubtedly had some rehydration which was masked due to the energy deficit of the therapy and no weight change was seen.

EXAMPLE IV

In mildly diarrheic calves, over the entire testing period, potassium concentration changes were evaluated one hour following therapy. Based on six evaluations on each calf they were slightly hyperkalemic prior to therapy shown in Table VIII. One hour following the invention therapy potassium level of all calves had dropped to within the normal range. The average decrease was 0.6 mEq/L.

The data included is set out in Table IX below.

TABLE IX

| | Potassium Concentration (mEq/L) changes due to therapy | 1 Hour Post | Mean Change |
|---|---|---|---|
| Invention | 5.1 ± 0.1 | 4.5 ± 0.1 | −0.6 |
| Prior Art U.S. Pat. No. 4,164,568 | 5.0 ± 0.1 | 4.8 ± 0.1 | −0.2 |

In the calves treated with the prior art formulation, the decrease in K was considerably less. On several occasions these mammals remained hyperkalemic. These changes were seen in spite of the higher potassium concentration in these treated with the formulation of the instant application.

EXAMPLE V

Figure 4:
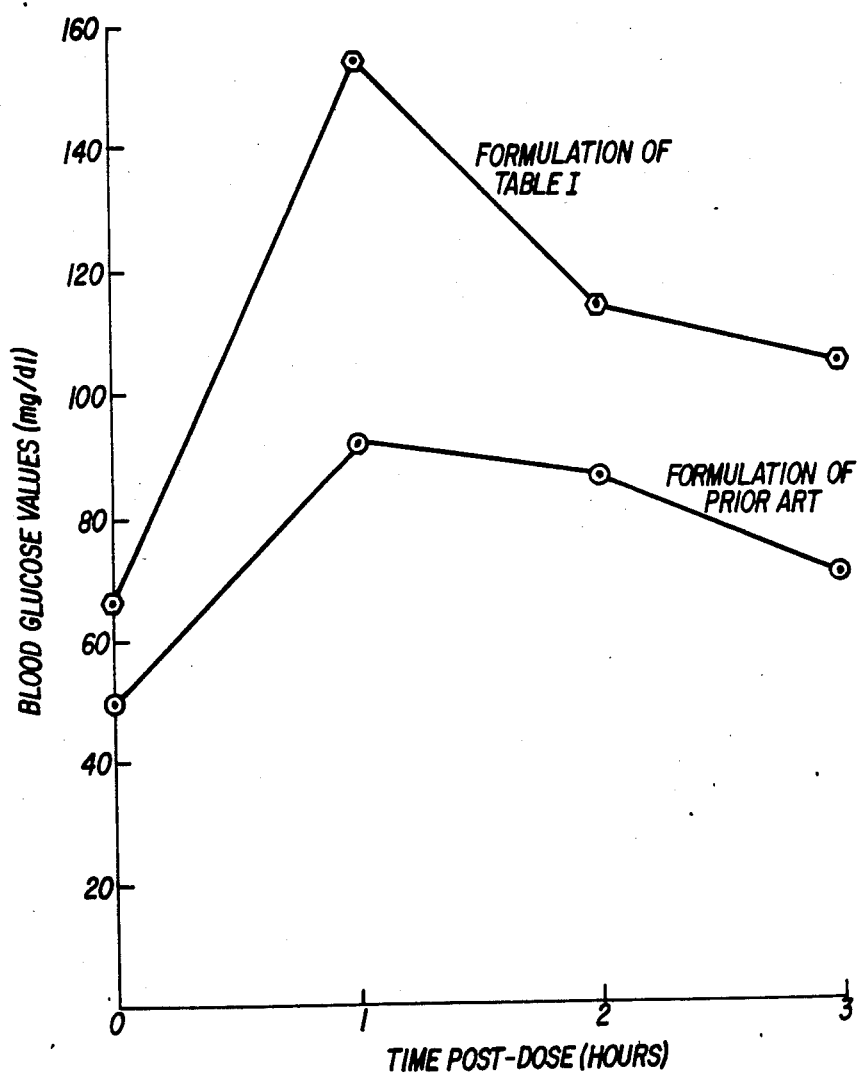
FIG. 4 is a graph showing changes in glucose concentration during 3 hours following therapy.

Prior to any therapy administration, all of the mildly diarrheic calves had low-normal blood glucose concentration averaging 78 and 71 mg/dl. In FIG. 4, changes in glucose concentration during the three hours following therapy have been plotted for calves treated with the formulation of the instant invention and those treated in the formulation of the prior art for a two-period period, or four treatments per calf, during the period of therapy alone, when the calves were receiving less than maintenance energy requirements. The calves treated with the formulation of the instant invention became slightly hypoglycemic between therapys dropping from a mean of 78 to a mean of 67 mg/dl. The calves treated with the prior formulation became severely hypoglycemic; they had entered the study with a mean blood glucose of 71 mg/dl, their pretherapy glucose concentration was 49 mg/dl during the time that they received the therapy.

The formulation of the instant invention produced a significantly greater plasma glucose response. Based on the area under the curve it was twice as great. Further, the calves treated with the formulation of the instant invention had high normal glucose concentration three hours following therapy while the prior art calves had already become hypoglycemic again (FIG. 1).

EXAMPLE VI

Further evidence substantiating the claim that the hyperosmotic nature of the formulation of the instant invention does not cause hemoconcentration can be gleaned from Table IX which represents the average change in hematocrit and plasma protein concentration one hour following therapy in mildly diarrheic calves treated with the formulation of the instant invention. On the average, the therapy elicited a minor hemodilution as evidenced by a decrease in both hematocrit and plasma protein concentrations. This establishes that the invention, in spite of its hyperosmolar natures does not cause excessive fluid secretion from the blood.

EXAMPLE VII

The effect of the therapy on blood gas and acid base status in mildly diarrheic calves is presented in Table XI below compared to prior art therapy. Although numerous reports attest to the prevalence of acidosis and decreased bicarbonate levels in more severe diarrhea, these mildly diarrheic calves had normal blood pH and essentially normal blood bicarbonate and base excess values. The calves treated with the formulation of the instant invention had a mean increase of 0.023 pH units compared to no change or a slight decrease (−0.005) pH units in the animals treated with the formulation of the prior art. They, in addition, with the formulation of the prior art had a decrease in total bicarbonate and no change in base excess. Thus, the therapy of the instant invention was able to change all of these important parameters of acid base status in a beneficial direction. That is, it increased alkalinity which is of important significance in treating diarrheic acidosis.

TABLE X

Therapy Induced Changes in Hematocrit and Plasma Protein Concentrations

| Therapy | # Calves | Pre-Therapy | 1 Hr. Post | Pre-Therapy | 1 Hr. Post |
|---|---|---|---|---|---|
| Day one 1 | 3 | 24.5 | 24.5 | 4.5 | 4.6 |
| 2 | 3 | 28.7 | 29.3 | 4.4 | 4.5 |
| Day two 3 | 3 | 30.0 | 28.7 | 4.4 | 4.5 |
| 4 | 3 | 29.3 | 28.7 | 4.5 | 4.4 |
| Day three 5 | 3 | 30.3 | 28.7 | 5.2 | 4.7 |
| 6 | 3 | 26.7 | 27.0 | 4.8 | 4.6 |
| Average | | 29.2 | 27.0 | 4.8 | 4.5 |

TABLE XI

Acid Base Changes due to Therapy*

| | Invention | U.S. Pat. No. 4,164,568 Prior Art Therapy |
|---|---|---|
| pH | | |
| Pre Therapy | 7.461 ± 0.007 | 7.470 ± 0.008 |
| Post Therapy (1 hour) | 7.484 ± 0.012 | 7.465 ± 0.005 |
| Change in pH | +0.023 | −0.005 |
| Total Bicarbonate | | |
| Pre Therapy | 24.9 ± 0.5 | 21.8 ± 0.5 |
| Post Therapy (1 hour) | 26.0 ± 0.5 | 21.1 ± 0.4 |
| Change in HCO$_3$ | +1.1 | −0.7 |
| Base Excess** | | |
| Changes in Base Excess 1 Hour After Therapy | +1.5 ± 0.3 | +0.1 ± 0.1 |

*Values shown are mean ± S.E.
**Base excess is a measure of total acidity and alkalinity. An increase in base excess indicates correction of acidosis.

Since modifications and variations of the invention as described hereinabove can be made without departing therefrom, the scope of the invention is to be limited only by the following claims.

What is claimed is:

1. A method of treating diarrhea in bovine animals comprising orally administering an aqueous solution of glucose, glycine, citric acid and a non-toxic alkali metal salt of acetic acid which will have an osmolality of 50 to 100 mOs as oxidized and is present in quantities greater than 0.5 percent of the solution.

2. The method according to claim 1, wherein the non-toxic alkali metal salts are sodium and potassium, and wherein the sum of the sodium and potassium cations equals 120 to 160 mOsm per liter, the potassium equals 10 to 30 mOsm per liter and the sodium equals 110 mOsm per liter.

3. An easily absorbed and metabolized veterinary composition for rapidly increasing the energy reserves of a mammal during an oral treatment for diarrhea comprising between approximately 70% and 90% by weight of a monosaccharide selected from the group consisting of glucose and galactose together with between approximately 3 percent and 12 percent by weight of a non-toxic alkali metal salt of acetic acid, a naturally occurring amino acid and water for producing a hypertonic alkaline solution ready for administration having an osmolality of approximately at least twice that of normal body osmolality containing between approximately 30 and 90 g/l of the monosaccharide and between approximately 40 and 120 mEq/l of bicarbonate whereby both maintenance and immediate energy are supplied to the mammal.

4. A veterinary composition according to claim 3 further including sodium and potassium with the sum of the sodium and potassium being 120 to 160 mOsm/l with the potassium being present as 10 to 30 mOsm/l and the sodium 110 to 150 mOsm/l.

5. The composition defined in claim 3 in which the osmolality of the solution is between approximately two and four times normal body osmolality.

6. The composition defined in claim 3 wherein said sodium acetate forms more than 6 percent of the composition.

7. A method of treating diarrhea in mammals which comprises the steps of first dissolving between approximately 70% and 90% by weight of a monosaccharide selected from the group consisting of glucose and galactose together with between approximately 3 percent and 12 percent by weight of a non-toxic alkali metal salt of acetic acid and a naturally occurring amino acid in water to produce a hypertonic alkaline solution having an osmolality at least approximately twice that of normal body osmolality containing between approximately 30 and 90 g/l of the monosaccharide and between approximately 40 and 120 mEq/l of bicarbonate and thereafter administering said solution orally to the diarrheic mammal.

8. The method defined in claim 7 in which the osmolality of the solution is between approximately two and four times normal body osmolality.

9. The method defined in claim 7 wherein the administered composition includes more than 6 percent sodium acetate.

10. An easily absorbed and metabolized veterinary composition for rapidly increasing the energy reserves and the bicarbonate level of a mammal in an oral treatment for diarrhea comprising a hypertonic alkaline solution having an osmolality of between approximately 600 and 1,200 mOsm/l and a bicarbonate concentration of between approximately 40 and 120 g/l resulting from the combination of between approximately 70 and 90% by weight of a monosaccharide selected from the group consisting of glucose and galactose together with between approximately 3 percent and 12 percent by weight of a non-toxic alkali metal salt of acetic acid and an amino acid dissolved in water to produce an aqueous solution containing between approximately 30 and 90 g/l of the monosaccharide.

11. A veterinary composition according to claim 10 further including energy substrates consisting of glucose, acetate, glycine and citric acid which provide 50 to 100 percent of the animal's energy requirements as they are metabolized.

12. The veterinary composition according to claim 11, wherein as the energy substrates are metabolized the remaining ions approximate an isoosmotic extracellular fluid.

13. A method of treating diarrhea in mammals comprising simultaneously increasing the amount of energy and the bicarbonate level in the mammal by orally administering a hypertonic alkaline solution having an osmolality of between approximately 600 and 1,200 mOsm/l and a bicarbonate concentration of between approximately 40 and 120 g/l achieved by combining between approximately 70 and 90% by weight of a monosaccharide selected from the group consisting of glucose and galactose with between approximately 3 percent and 12 percent by weight of a non-toxic alkali metal salt of acetic acid and an amino acid to produce a solution upon being dissolved in water containing between approximately 30 and 90 g/l of the monosaccharide.

14. In a veterinary composition useful for the treatment of diarrhea in mammals of the type which includes a water soluble monosaccharide and an amino acid, the improvement which comprises incorporating into the composition a sufficient quantity of a non-toxic alkali metal salt of acetic acid effective when diluted with water for administration along with the other water soluble components to provide at least approximately 40 mEq/l of bicarbonate.

15. The veterinary composition according to claim 14 in which the quantity of the alkali metal salt of acetic acid included in the composition is effective when diluted with water for administration to provide between approximately 40 and 160 mEq/l of bicarbonate.

16. A veterinary composition useful for the treatment of diarrhea in mammals which comprises: between approximately 70 and 90 percent by weight of an actively absorbed monosaccharide together with between approximately 1 percent and 7.5 percent by weight of an actively absorbed naturally occurring amino acid and between approximately 3 and 12 percent by weight of a non-toxic alkali metal salt of acetic acid for providing a concentration of the monosaccharide of between approximately 30 and 90 grams per liter in a hypertonic alkaline solution having an osmolality at least twice that of normal body osmolality.

17. The veterinary composition as set forth in claim 16 in which the osmolality of the dilute hypertonic alkaline solution ready for administration is between approximately two and four times that of normal body osmolality.

18. The veterinary composition as set forth in claim 16 in which the osmolality of the dilute hypertonic alkaline solution ready for administration is between approximately 600 and 1,200 mOsm/l.

19. In the method for treating diarrhea in mammals which includes the administration of an essentially isotonic aqueous solution containing a monosaccharide and an amino acid, the improvement which comprises providing a concentration of the monosaccharide in the dilute solution ready for administration at a level where it is hypertonic and has an osmolality at least approximately twice that of normal body osmolality.

20. The improved method for treating diarrhea in mammals as set forth in claim 19 in which the osmolality of the hypertonic solution ready for administration is between approximately two and four times that of normal body osmolality.

21. The improved method for treating diarrhea in mammals as set forth in claim 20 in which the osmolality of the hypertonic solution ready for administration is between approximately 600 and 1,200 mOsm/l.

22. In the method for treating diarrhea in mammals which includes the administration of an essentially acidic solution containing a monosaccharide and an amino acid, the improvement which comprises alkalizing the composition when diluted preparatory to administration through the incorporation of a non-toxic alkali metal salt of acetic acid in sufficient quantities to produce at least approximately 40 mEq/l of bicarbonate.

23. The improved method for treating diarrhea in mammals as set forth in claim 22 in which the concentration of the alkali metal salt is sufficient to produce between approximately 40 and 120 mEq/l of bicarbonate.

* * * * *